United States Patent
Druker et al.

(10) Patent No.: US 7,592,142 B2
(45) Date of Patent: *Sep. 22, 2009

(54) DETECTION OF GLEEVEC RESISTANCE

(75) Inventors: Brian J. Druker, Portland, OR (US); Amie Corbin, Portland, OR (US)

(73) Assignee: Oregon Health and Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/178,926

(22) Filed: Jul. 24, 2008

(65) Prior Publication Data

US 2008/0305492 A1    Dec. 11, 2008

Related U.S. Application Data

(60) Continuation of application No. 11/873,985, filed on Oct. 17, 2007, now Pat. No. 7,416,873, which is a division of application No. 11/524,626, filed on Sep. 20, 2006, now Pat. No. 7,326,534, which is a continuation of application No. 11/343,891, filed on Jan. 31, 2006, now abandoned, which is a continuation of application No. 10/263,480, filed on Oct. 3, 2002, now abandoned.

(60) Provisional application No. 60/327,387, filed on Oct. 5, 2001.

(51) Int. Cl.
*C12Q 1/68*    (2006.01)
(52) U.S. Cl. .......................................................... 435/6
(58) Field of Classification Search ...................... 435/6
See application file for complete search history.

(56) References Cited

U.S. PATENT DOCUMENTS

2003/0158105 A1    8/2003    Sawyers et al.

FOREIGN PATENT DOCUMENTS

WO    WO 97/08184    3/1997

OTHER PUBLICATIONS

Barthe et al., "Roots of Clinical Resistance to STI-571 Cancer Therapy," *Science* 293(5538):3 pages—2163a (2001).
Corbin et al., "Analysis of the Structural Basis of Specificity of Inhibition of Abl Kinase by STI571," *Am. Soc. Hematol.* Washington DC (2000)—Abstract.
Druker et al., "Activity of a Specific Inhibitor of the BCR-ABL Tyrosine Kinase in the Blast Crisis of Chronic Myeloid Leukemia and Acute Lymphoblastic Leukemia with the Philadelphia Chromosome," *N. Engl. J. Med.* 344(14):1038-1042 (2001).
Druker et al., "Effects of a selective inhibitor of the Abl tyrosine kinase on the growth of Bcr-Abl positive cells," *Nature Medicine* 2(5):561-566 (1996).
Gorre et al., "Clinical Resistance to STI-571 Cancer Therapy Caused by BCR-ABL Gene Mutation or Amplification," *Science* 293(5531):879-880 (2001).
Hockhaus et al., "Roots of Clinical Resistance to STI-571 Cancer Therapy," *Science* 293(5538):3 pages—2163a (2001).
Hofmann et al., "Ph+ Acute Lymphoblastic Leukemias Resistant to STI571 (Glivec) Have a Novel and Unique BCR-ABL Gene Mutation," *Am. Soc. Hematol.* Washington DC (2001)—Abstract.
Warmuth et al., "Genetic Analysis of the ATP Binding Sites of HCK and ABL Kinases Reveal Distinct and Overlapping Determinants for the Specficity of the Tyrosine Kinase Inhibitors PP1 and STI571," *Am. Soc. Hematol.*, Washington DC (2000)—Abstract.

*Primary Examiner*—Maryam Monshipouri
(74) *Attorney, Agent, or Firm*—Klarquist Sparkman, LLP

(57) ABSTRACT

The present invention relates to isolated polypeptides which comprise an amino acid sequence consisting of a mutated functional Abl kinase domain, said mutated functional kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof, to the use of such polypeptides to screen for compounds which inhibit the tyrosine kinase activity of such polypeptides, to nucleic acid molecules encoding such polypeptides, to recombinant vectors and host cells comprising such nucleic acid molecules and to the use of such nucleic acid molecules in the production of such polypeptides for use in screening for compounds which inhibit the tyrosine kinase activity of such polypeptides.

25 Claims, No Drawings

SEQUENCE LISTING

<160> NUMBER OF SEQ ID NOS: 2

<210> SEQ ID NO 1
<211> LENGTH: 3393
<212> TYPE: DNA
<213> ORGANISM: Homo sapiens
<220> FEATURE:
<221> NAME/KEY: CDS
<222> LOCATION: (1)..(3393)

<400> SEQUENCE: 1

```
atg ttg gag atc tgc ctg aag ctg gtg ggc tgc aaa tcc aag aag ggg      48
Met Leu Glu Ile Cys Leu Lys Leu Val Gly Cys Lys Ser Lys Lys Gly
1               5                   10                  15 ctg tcc tcg tcc tcc agc tgt tat ctg gaa gaa gcc ctt cag cgg cca      96
Leu Ser Ser Ser Ser Ser Cys Tyr Leu Glu Glu Ala Leu Gln Arg Pro
            20                  25                  30 gta gca tct gac ttt gag cct cag ggt ctg agt gaa gcc gct cgt tgg     144
Val Ala Ser Asp Phe Glu Pro Gln Gly Leu Ser Glu Ala Ala Arg Trp
35                  40                  45 aac tcc aag gaa aac ctt ctc gct gga ccc agt gaa aat gac ccc aac     192
Asn Ser Lys Glu Asn Leu Leu Ala Gly Pro Ser Glu Asn Asp Pro Asn
    50                  55                  60 ctt ttc gtt gca ctg tat gat ttt gtg gcc agt gga gat aac act cta     240
Leu Phe Val Ala Leu Tyr Asp Phe Val Ala Ser Gly Asp Asn Thr Leu
65                  70                  75                  80 agc ata act aaa ggt gaa aag ctc cgg gtc tta ggc tat aat cac aat     288
Ser Ile Thr Lys Gly Glu Lys Leu Arg Val Leu Gly Tyr Asn His Asn
                85                  90                  95 ggg gaa tgg tgt gaa gcc caa acc aaa aat ggc caa ggc tgg gtc cca     336
Gly Glu Trp Cys Glu Ala Gln Thr Lys Asn Gly Gln Gly Trp Val Pro
            100                 105                 110 agc aac tac atc acg cca gtc aac agt ctg gag aaa cac tcc tgg tac     384
Ser Asn Tyr Ile Thr Pro Val Asn Ser Leu Glu Lys His Ser Trp Tyr
115                 120                 125 cat ggg cct gtg tcc cgc aat gcc gct gag tat ctg ctg agc agc ggg     432
His Gly Pro Val Ser Arg Asn Ala Ala Glu Tyr Leu Leu Ser Ser Gly
130                 135                 140 atc aat ggc agc ttc ttg gtg cgt gag agt gag agc agt cct ggc cag     480
Ile Asn Gly Ser Phe Leu Val Arg Glu Ser Glu Ser Ser Pro Gly Gln
145                 150                 155                 160 agg tcc atc tcg ctg aga tac gaa ggg agg gtg tac cat tac agg atc     528
Arg Ser Ile Ser Leu Arg Tyr Glu Gly Arg Val Tyr His Tyr Arg Ile
                165                 170                 175 aac act gct tct gat ggc aag ctc tac gtc tcc tcc gag agc cgc ttc     576
Asn Thr Ala Ser Asp Gly Lys Leu Tyr Val Ser Ser Glu Ser Arg Phe
            180                 185                 190 aac acc ctg gcc gag ttg gtt cat cat cat tca acg gtg gcc gac ggg     624
Asn Thr Leu Ala Glu Leu Val His His His Ser Thr Val Ala Asp Gly
195                 200                 205 ctc atc acc acg ctc cat tat cca gcc cca aag cgc aac aag ccc act     672
Leu Ile Thr Thr Leu His Tyr Pro Ala Pro Lys Arg Asn Lys Pro Thr
210                 215                 220 gtc tat ggt gtg tcc ccc aac tac gac aag tgg gag atg gaa cgc acg     720
Val Tyr Gly Val Ser Pro Asn Tyr Asp Lys Trp Glu Met Glu Arg Thr
225                 230                 235                 240 gac atc acc atg aag cac aag ctg ggg ggc cag tac ggg gag gtg         768
Asp Ile Thr Met Lys His Lys Leu Gly Gly Gln Tyr Gly Glu Val
245                 250                 255 tac gag ggc gtg tgg aag aaa tac agc ctg acg gtg gcc gtg aag acc     816
Tyr Glu Gly Val Trp Lys Lys Tyr Ser Leu Thr Val Ala Val Lys Thr
260                 265                 270 ttg aag gag gac acc atg gag gtg gaa gag ttc ttg aaa gaa gct gca     864
Leu Lys Glu Asp Thr Met Glu Val Glu Glu Phe Leu Lys Glu Ala Ala
275                 280                 285 gtc atg aaa gag atc aaa cac cct aac ctg gtg cag ctc ctt ggg gtc     912
Val Met Lys Glu Ile Lys His Pro Asn Leu Val Gln Leu Leu Gly Val
290                 295                 300
```

```
tgc acc cgg gag ccc ccg ttc tat atc atc act gag ttc atg acc tac    960
Cys Thr Arg Glu Pro Pro Phe Tyr Ile Ile Thr Glu Phe Met Thr Tyr
305                 310                 315                 320 ggg aac ctc ctg gac tac ctg agg gag tgc aac cgg cag gag gtg aac   1008
Gly Asn Leu Leu Asp Tyr Leu Arg Glu Cys Asn Arg Gln Glu Val Asn
    325                 330                 335 gcc gtg gtg ctg ctg tac atg gcc act cag atc tcg tca gcc atg gag   1056
Ala Val Val Leu Leu Tyr Met Ala Thr Gln Ile Ser Ser Ala Met Glu
340                 345                 350 tac ctg gag aag aaa aac ttc atc cac aga gat ctt gct gcc cga aac   1104
Tyr Leu Glu Lys Lys Asn Phe Ile His Arg Asp Leu Ala Ala Arg Asn
355                 360                 365 tgc ctg gta ggg gag aac cac ttg gtg aag gta gct gat ttt ggc ctg   1152
Cys Leu Val Gly Glu Asn His Leu Val Lys Val Ala Asp Phe Gly Leu
370                 375                 380 agc agg ttg atg aca ggg gac acc tac aca gcc cat gct gga gcc aag   1200
Ser Arg Leu Met Thr Gly Asp Thr Tyr Thr Ala His Ala Gly Ala Lys
385                 390                 395                 400 ttc ccc atc aaa tgg act gca ccc gag agc ctg gcc tac aac aag ttc   1248
Phe Pro Ile Lys Trp Thr Ala Pro Glu Ser Leu Ala Tyr Asn Lys Phe
405                 410                 415 tcc atc aag tcc gac gtc tgg gca ttt gga gta ttg ctt tgg gaa att   1296
Ser Ile Lys Ser Asp Val Trp Ala Phe Gly Val Leu Leu Trp Glu Ile
420                 425                 430 gct acc tat ggc atg tcc cct tac ccg gga att gac ctg tcc cag gtg   1344
Ala Thr Tyr Gly Met Ser Pro Tyr Pro Gly Ile Asp Leu Ser Gln Val
435                 440                 445 tat gag ctg cta gag aag gac tac cgc atg gag cgc cca gaa ggc tgc   1392
Tyr Glu Leu Leu Glu Lys Asp Tyr Arg Met Glu Arg Pro Glu Gly Cys
450                 455                 460 cca gag aag gtc tat gaa ctc atg cga gca tgt tgg cag tgg aat ccc   1440
Pro Glu Lys Val Tyr Glu Leu Met Arg Ala Cys Trp Gln Trp Asn Pro
465                 470                 475                 480 tct gac cgg ccc tcc ttt gct gaa atc cac caa gcc ttt gaa aca atg   1488
Ser Asp Arg Pro Ser Phe Ala Glu Ile His Gln Ala Phe Glu Thr Met
485                 490                 495 ttc cag gaa tcc agt atc tca gac gaa gtg gaa aag gag ctg ggg aaa   1536
Phe Gln Glu Ser Ser Ile Ser Asp Glu Val Glu Lys Glu Leu Gly Lys
500                 505                 510 caa ggc gtc cgt ggg gct gtg agt acc ttg ctg cag gcc cca gag ctg   1584
Gln Gly Val Arg Gly Ala Val Ser Thr Leu Leu Gln Ala Pro Glu Leu
515                 520                 525 ccc acc aag acg agg acc tcc agg aga gct gca gag cac aga gac acc   1632
Pro Thr Lys Thr Arg Thr Ser Arg Arg Ala Ala Glu His Arg Asp Thr
530                 535                 540 act gac gtg cct gag atg cct cac tcc aag ggc cag gga gag agc gat   1680
Thr Asp Val Pro Glu Met Pro His Ser Lys Gly Gln Gly Glu Ser Asp
545                 550                 555                 560 cct ctg gac cat gag cct gcc gtg tct cca ttg ctc cct cga aaa gag   1728
Pro Leu Asp His Glu Pro Ala Val Ser Pro Leu Leu Pro Arg Lys Glu
565                 570                 575 cga ggt ccc ccg gag ggc ggc ctg aat gaa gat gag cgc ctt ctc ccc   1776
Arg Gly Pro Pro Glu Gly Gly Leu Asn Glu Asp Glu Arg Leu Leu Pro
580                 585                 590 aaa gac aaa aag acc aac ttg ttc agc gcc ttg atc aag aag aag aag   1824
Lys Asp Lys Lys Thr Asn Leu Phe Ser Ala Leu Ile Lys Lys Lys Lys
595                 600                 605 aag aca gcc cca acc cct ccc aaa cgc agc agc tcc ttc cgg gag atg   1872
Lys Thr Ala Pro Thr Pro Pro Lys Arg Ser Ser Ser Phe Arg Glu Met
610                 615                 620
```

-continued

| | |
|---|---|
| gac ggc cag ccg gag cgc aga ggg gcc ggc gag gaa gag ggc cga gac<br>Asp Gly Gln Pro Glu Arg Arg Gly Ala Gly Glu Glu Glu Gly Arg Asp<br>625                                      630                            635                            640 | 1920 |
| atc agc aac ggg gca ctg gct ttc acc ccc ttg gac aca gct gac cca<br>Ile Ser Asn Gly Ala Leu Ala Phe Thr Pro Leu Asp Thr Ala Asp Pro<br>645                                      650                            655 | 1968 |
| gcc aag tcc cca aag ccc agc aat ggg gct ggg gtc ccc aat gga gcc<br>Ala Lys Ser Pro Lys Pro Ser Asn Gly Ala Gly Val Pro Asn Gly Ala<br>660                                  665                              670 | 2016 |
| ctc cgg gag tcc ggg ggc tca ggc ttc cgg tct ccc cac ctg tgg aag<br>Leu Arg Glu Ser Gly Gly Ser Gly Phe Arg Ser Pro His Leu Trp Lys<br>675                                  680                            685 | 2064 |
| aag tcc agc acg ctg acc agc agc cgc cta gcc acc ggc gag gag gag<br>Lys Ser Ser Thr Leu Thr Ser Ser Arg Leu Ala Thr Gly Glu Glu Glu<br>690                                  695                            700 | 2112 |
| ggc ggt ggc agc tcc agc aag cgc ttc ctg cgc tct tgc tcc gcc tcc<br>Gly Gly Gly Ser Ser Ser Lys Arg Phe Leu Arg Ser Cys Ser Ala Ser<br>705                                  710                            715                            720 | 2160 |
| tgc gtt ccc cat ggg gcc aag gac acg gag tgg agg tca gtc acg ctg<br>Cys Val Pro His Gly Ala Lys Asp Thr Glu Trp Arg Ser Val Thr Leu<br>725                                  730                            735 | 2208 |
| cct cgg gac ttg cag tcc acg gga aga cag ttt gac tcg tcc aca ttt<br>Pro Arg Asp Leu Gln Ser Thr Gly Arg Gln Phe Asp Ser Ser Thr Phe<br>740                                  745                            750 | 2256 |
| gga ggg cac aaa agt gag aag ccg gct ctg cct cgg aag agg gca ggg<br>Gly Gly His Lys Ser Glu Lys Pro Ala Leu Pro Arg Lys Arg Ala Gly<br>755                                  760                            765 | 2304 |
| gag aac agg tct gac cag gtg acc cga ggc aca gta acg cct ccc ccc<br>Glu Asn Arg Ser Asp Gln Val Thr Arg Gly Thr Val Thr Pro Pro Pro<br>770                                  775                            780 | 2352 |
| agg ctg gtg aaa aag aat gag gaa gct gct gat gag gtc ttc aaa gac<br>Arg Leu Val Lys Lys Asn Glu Glu Ala Ala Asp Glu Val Phe Lys Asp<br>785                                  790                            795                            800 | 2400 |
| atc atg gag tcc agc ccg ggc tcc agc ccg ccc aac ctg act cca aaa<br>Ile Met Glu Ser Ser Pro Gly Ser Ser Pro Pro Asn Leu Thr Pro Lys<br>805                                  810                            815 | 2448 |
| ccc ctc cgg cgg cag gtc acc gtg gcc cct gcc tcg ggc ctc ccc cac<br>Pro Leu Arg Arg Gln Val Thr Val Ala Pro Ala Ser Gly Leu Pro His<br>820                                  825                            830 | 2496 |
| aag gaa gaa gct gaa aag ggc agt gcc tta ggg acc cct gct gca gct<br>Lys Glu Glu Ala Glu Lys Gly Ser Ala Leu Gly Thr Pro Ala Ala Ala<br>835                                  840                            845 | 2544 |
| gag cca gtg acc ccc acc agc aaa gca ggc tca ggt gca cca ggg ggc<br>Glu Pro Val Thr Pro Thr Ser Lys Ala Gly Ser Gly Ala Pro Gly Gly<br>850                                  855                            860 | 2592 |
| acc agc aag ggc ccc gcc gag gag tcc aga gtg agg agg cac aag cac<br>Thr Ser Lys Gly Pro Ala Glu Glu Ser Arg Val Arg Arg His Lys His<br>865                                  870                            875                            880 | 2640 |
| tcc tct gag tcg cca ggg agg gac aag ggg aaa ttg tcc agg ctc aaa<br>Ser Ser Glu Ser Pro Gly Arg Asp Lys Gly Lys Leu Ser Arg Leu Lys<br>885                                  890                            895 | 2688 |
| cct gcc ccg ccg ccc cca cca gca gcc tct gca ggg aag gct gga gga<br>Pro Ala Pro Pro Pro Pro Ala Ala Ser Ala Gly Lys Ala Gly Gly<br>900                                  905                            910 | 2736 |
| aag ccc tcg cag agc ccg agc cag gag gcg gcc ggg gag gca gtc ctg<br>Lys Pro Ser Gln Ser Pro Ser Gln Glu Ala Ala Gly Glu Ala Val Leu<br>915                                  920                            925 | 2784 |
| ggc gca aag aca aaa gcc acg agt ctg gtt gat gct gtg aac agt gac<br>Gly Ala Lys Thr Lys Ala Thr Ser Leu Val Asp Ala Val Asn Ser Asp<br>930                                  935                            940 | 2832 |

```
gct gcc aag ccc agc cag ccg gga gag ggc ctc aaa aag ccc gtg ctc     2880
Ala Ala Lys Pro Ser Gln Pro Gly Glu Gly Leu Lys Lys Pro Val Leu
945                 950                 955                 960 ccg gcc act cca aag cca cag tcc gcc aag ccg tcg ggg acc ccc atc     2928
Pro Ala Thr Pro Lys Pro Gln Ser Ala Lys Pro Ser Gly Thr Pro Ile
            965                 970                 975 agc cca gcc ccc gtt ccc tcc acg ttg cca tca gca tcc tcg gcc ctg     2976
Ser Pro Ala Pro Val Pro Ser Thr Leu Pro Ser Ala Ser Ser Ala Leu
980                 985                 990 gca ggg gac cag ccg tct tcc act  gcc ttc atc cct ctc  ata tca acc   3024
Ala Gly Asp Gln Pro Ser Ser Thr  Ala Phe Ile Pro Leu  Ile Ser Thr
995                 1000                 1005 cga gtg tct ctt cgg aaa acc cgc cag cct cca gag cgg atc gcc         3069
Arg Val Ser Leu Arg Lys Thr Arg Gln Pro Pro Glu Arg Ile Ala
1010            1015                1020 agc ggc gcc atc acc aag ggc gtg gtc ctg gac agc acc gag gcg         3114
Ser Gly Ala Ile Thr Lys Gly Val Val Leu Asp Ser Thr Glu Ala
1025            1030                1035 ctg tgc ctc gcc atc tct agg aac tcc gag cag atg gcc agc cac         3159
Leu Cys Leu Ala Ile Ser Arg Asn Ser Glu Gln Met Ala Ser His
1040            1045                1050 agc gca gtg ctg gag gcc ggc aaa aac ctc tac acg ttc tgc gtg         3204
Ser Ala Val Leu Glu Ala Gly Lys Asn Leu Tyr Thr Phe Cys Val
1055            1060                1065 agc tat gtg gat tcc atc cag caa atg agg aac aag ttt gcc ttc         3249
Ser Tyr Val Asp Ser Ile Gln Gln Met Arg Asn Lys Phe Ala Phe
1070            1075                1080 cga gag gcc atc aac aaa ctg gag aat aat ctc cgg gag ctt cag         3294
Arg Glu Ala Ile Asn Lys Leu Glu Asn Asn Leu Arg Glu Leu Gln
1085            1090                1095 atc tgc ccg gcg aca gca ggc agt ggt ccg gcg gcc act cag gac         3339
Ile Cys Pro Ala Thr Ala Gly Ser Gly Pro Ala Ala Thr Gln Asp
1100            1105                1110 ttc agc aag ctc ctc agt tcg gtg aag gaa atc agt gac ata gtg         3384
Phe Ser Lys Leu Leu Ser Ser Val Lys Glu Ile Ser Asp Ile Val
1115            1120                1125 cag agg tag                                                         3393
Gln Arg
1130

<210> SEQ ID NO 2
<211> LENGTH: 1130
<212> TYPE: PRT
<213> ORGANISM: Homo sapiens

<400> SEQUENCE: 2

Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
20                  25                  30

Val Ala Ser Asp Phe Glu Pro Gln Gly Leu Ser Glu Ala Ala Arg Trp
35                  40                  45

Asn Ser Lys Glu Asn Leu Leu Ala Gly Pro Ser Glu Asn Asp Pro Asn
50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
85                  90                  95
```

```
Gly Glu Trp Cys Glu Ala Gln Thr Lys Asn Gly Gln Gly Trp Val Pro
100                 105                 110

Ser Asn Tyr Ile Thr Pro Val Asn Ser Leu Glu Lys His Ser Trp Tyr
115                 120                 125

His Gly Pro Val Ser Arg Asn Ala Ala Glu Tyr Leu Leu Ser Ser Gly
130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
165                 170                 175

Asn Thr Ala Ser Asp Gly Lys Leu Tyr Val Ser Ser Glu Ser Arg Phe
180                 185                 190

Asn Thr Leu Ala Glu Leu Val His His His Ser Thr Val Ala Asp Gly
195                 200                 205

Leu Ile Thr Thr Leu His Tyr Pro Ala Pro Lys Arg Asn Lys Pro Thr
210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gln Tyr Gly Glu Val
245                 250                 255

Tyr Glu Gly Val Trp Lys Lys Tyr Ser Leu Thr Val Ala Val Lys Thr
260                 265                 270

Leu Lys Glu Asp Thr Met Glu Val Glu Glu Phe Leu Lys Glu Ala Ala
275                 280                 285

Val Met Lys Glu Ile Lys His Pro Asn Leu Val Gln Leu Leu Gly Val
290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
325                 330                 335

Ala Val Val Leu Leu Tyr Met Ala Thr Gln Ile Ser Ser Ala Met Glu
340                 345                 350

Tyr Leu Glu Lys Lys Asn Phe Ile His Arg Asp Leu Ala Ala Arg Asn
355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
405                 410                 415

Ser Ile Lys Ser Asp Val Trp Ala Phe Gly Val Leu Leu Trp Glu Ile
420                 425                 430

Ala Thr Tyr Gly Met Ser Pro Tyr Pro Gly Ile Asp Leu Ser Gln Val
435                 440                 445

Tyr Glu Leu Leu Glu Lys Asp Tyr Arg Met Glu Arg Pro Glu Gly Cys
450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
485                 490                 495

Phe Gln Glu Ser Ser Ile Ser Asp Glu Val Glu Lys Glu Leu Gly Lys
500                 505                 510
```

```
Gln Gly Val Arg Gly Ala Val Ser Thr Leu Leu Gln Ala Pro Glu Leu
515                 520                 525

Pro Thr Lys Thr Arg Thr Ser Arg Arg Ala Ala Glu His Arg Asp Thr
530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
565                 570                 575

Arg Gly Pro Pro Glu Gly Gly Leu Asn Glu Asp Glu Arg Leu Leu Pro
580                 585                 590

Lys Asp Lys Lys Thr Asn Leu Phe Ser Ala Leu Ile Lys Lys Lys Lys
595                 600                 605

Lys Thr Ala Pro Thr Pro Pro Lys Arg Ser Ser Ser Phe Arg Glu Met
610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
645                 650                 655

Ala Lys Ser Pro Lys Pro Ser Asn Gly Ala Gly Val Pro Asn Gly Ala
660                 665                 670

Leu Arg Glu Ser Gly Gly Ser Gly Phe Arg Ser Pro His Leu Trp Lys
675                 680                 685

Lys Ser Ser Thr Leu Thr Ser Ser Arg Leu Ala Thr Gly Glu Glu Glu
690                 695                 700

Gly Gly Gly Ser Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
725                 730                 735

Pro Arg Asp Leu Gln Ser Thr Gly Arg Gln Phe Asp Ser Ser Thr Phe
740                 745                 750

Gly Gly His Lys Ser Glu Lys Pro Ala Leu Pro Arg Lys Arg Ala Gly
755                 760                 765

Glu Asn Arg Ser Asp Gln Val Thr Arg Gly Thr Val Thr Pro Pro Pro
770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Asn Leu Thr Pro Lys
805                 810                 815

Pro Leu Arg Arg Gln Val Thr Val Ala Pro Ala Ser Gly Leu Pro His
820                 825                 830

Lys Glu Glu Ala Glu Lys Gly Ser Ala Leu Gly Thr Pro Ala Ala Ala
835                 840                 845

Glu Pro Val Thr Pro Thr Ser Lys Ala Gly Ser Gly Ala Pro Gly Gly
850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
885                 890                 895

Pro Ala Pro Pro Pro Pro Ala Ala Ser Ala Gly Lys Ala Gly Gly
900                 905                 910

Lys Pro Ser Gln Ser Pro Ser Gln Glu Ala Ala Gly Glu Ala Val Leu
915                 920                 925
```

-continued

```
Gly Ala Lys Thr Lys Ala Thr Ser Leu Val Asp Ala Val Asn Ser Asp
930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
965                 970                 975

Ser Pro Ala Pro Val Pro Ser Thr Leu Pro Ser Ala Ser Ser Ala Leu
980                 985                 990

Ala Gly Asp Gln Pro Ser Ser Thr  Ala Phe Ile Pro Leu  Ile Ser Thr
995                 1000                1005

Arg Val  Ser Leu Arg Lys Thr  Arg Gln Pro Pro Glu  Arg Ile Ala
1010                1015                1020

Ser Gly  Ala Ile Thr Lys Gly  Val Val Leu Asp Ser  Thr Glu Ala
1025                1030                1035

Leu Cys  Leu Ala Ile Ser Arg  Asn Ser Glu Gln Met  Ala Ser His
1040                1045                1050

Ser Ala  Val Leu Glu Ala Gly  Lys Asn Leu Tyr Thr  Phe Cys Val
1055                1060                1065

Ser Tyr  Val Asp Ser Ile Gln  Gln Met Arg Asn Lys  Phe Ala Phe
1070                1075                1080

Arg Glu  Ala Ile Asn Lys Leu  Glu Asn Asn Leu Arg  Glu Leu Gln
1085                1090                1095

Ile Cys  Pro Ala Thr Ala Gly  Ser Gly Pro Ala Ala  Thr Gln Asp
1100                1105                1110

Phe Ser  Lys Leu Leu Ser Ser  Val Lys Glu Ile Ser  Asp Ile Val
1115                1120                1125

Gln Arg
1130
```

DETECTION OF GLEEVEC RESISTANCE

CROSS REFERENCE TO RELATED APPLICATIONS

This application is a continuation of U.S. patent application Ser. No. 11/873,985, filed Oct. 17, 2007, now U.S. Pat. No. 7,416,873 which is a divisional of U.S. patent application Ser. No. 11/524,626, filed Sep. 20, 2006, now U.S. Pat. No. 7,326,534, issued Feb. 5, 2008, which is a continuation of U.S. patent application Ser. No. 11/343,891, filed Jan. 31, 2006, now abandoned which is a continuation of U.S. patent application Ser. No. 10/263,480, filed Oct. 3, 2002 now abandoned. U.S. patent application Ser. No. 10/263,480 claims the benefit of U.S. Provisional Application No. 60/327,387, filed Oct. 5, 2001. U.S. patent application Ser. Nos. 11/873,985, 11/524,626, and 11/343,891 are incorporated herein by reference in their entity.

FIELD OF THE INVENTION

This invention relates to isolated polypeptides which comprise an amino acid sequence consisting of a mutated functional Abl kinase domain, said mutated functional kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof, to the use of such polypeptides to screen for compounds which inhibit the tyrosine kinase activity of such polypeptides, to nucleic add molecules encoding such polypeptides, to recombinant vectors and host cells comprising such nucleic acid molecules and to the use of such nucleic acid molecules in the production of such polypeptides for use in screening for compounds which inhibit the tyrosine kinase activity of such polypeptides.

BACKGROUND OF THE INVENTION

Bcr-Abl, a constitutively activated tyrosine kinase resulting from the formation of the Philadelphia chromosome [Nowell P. C. and Hungerford D. A., Science 132, 1497 (1960)] by reciprocal translocation between the long arms of chromosomes 9 and 22 [Rowley J. D., Nature 243, 290-293 (1973)], has been established as the characteristic molecular abnormality present in virtually all cases of chronic myeloid leukemia (CML) and up to 20 percent of adult acute lymphoblastic leukemia (ALL) [Faderl S. et al., N Engl J Med 341, 164-172 (1999); Sawyers C. L., N Engl J Med 340, 1330-1340 (1999)]. Bcr-Abl is sufficient to cause CML in mice [Daley G. Q. et al., Science 247, 824-830 (1990)] and its transforming capacity is absolutely dependent on tyrosine kinase activity [Lugo T. G. et al., Science 247, 1079 (1990)]. The compound N-[4-methyl-3-(4-pyridin-3-yl-pyrimidin-2-ylamino)-phenyl]-4-(4-methyl-piperazin-1-ylmethyl)-benzamide (hereinafter also referred to as "STI571"; STI571 is described in EP-0 564 409 and, in the form of the methane sulfonate salt, in WO 99/03854), a competitive inhibitor at the ATP-binding site of Bcr-Abl, as well as of the receptor for platelet-derived growth factor, and c-kit tyrosine kinase [Lugo T. G. et al., Science 247, 1079 (1990)], has been shown to be capable of very rapidly reversing the clinical and hematological abnormalities of CML in chronic phase and in blast crisis as well as of Ph-chromosome-positive (Ph+) acute lymphoblastic leukemia (Ph+ALL) [Druker B. J. et al., N Engl J Med 344, 1031-1037 (2001); Druker B. J. et al., N Engl J Med 344, 1038-1042 (2001)]. Whereas almost all chronic phase CML patients durably respond, remissions in CML blast crisis and Ph+ ALL are transient, and most patients relapse after several months, despite continued therapy with STI571 [Druker B. J. et al., N Engl J Med 344, 1038-1042 (2001)]. The mechanism of resistance to STI571 is subject of intense research.

It was now surprisingly found that mutations present in the kinase domain of the Bcr-Abl gene of patients suffering from CML or Ph+ ALL account for the biological resistance of these patients towards STI571 treatment in that said mutations lead to resistance of the Bcr-Abl tyrosine kinase towards inhibition by STI571.

These findings are extremely valuable in e.g. finding new compounds or combinations of compounds which are capable to overcome resistance towards treatment with STI571. Moreover, knowledge of such mutations is also very useful in the diagnosis of Ph+ leukemias in that it allows e.g. the detection of drug-resistant clones before clinical relapse of the patient.

DEFINITIONS

Within the context of this disclosure the following expressions, terms and abbreviations have the meanings as defined below:

In the expression "a mutated functional Abl kinase domain", the part "mutated Abl kinase domain" refers to the native human Abl kinase domain containing mutations including amino acid exchanges, amino acid deletions and/or amino acid additions.

In the expression "a mutated functional Abl kinase domain", the term "functional" indicates that the respective kinase domain possesses tyrosine kinase activity. Preferably, the kinase activity of the mutated functional Abl kinase domain is in the range of that of the native human Abl kinase domain.

In the expression "a mutated functional Abl kinase domain being resistant to inhibition of its tyrosine kinase activity by STI571 or a salt thereof", the term "resistant" means that STI571 inhibits the respective mutated functional Abl kinase domain with an $IC_{50}$ that is higher than that of the native human Abl kinase domain, i.e. higher than about 0.025 µM, preferably higher than about 0.15 µM, more preferably higher than about 0.25 µM, most preferably higher than about 5 µM.

In the expression "amino acid sequence of the native human Abl kinase domain or an essentially similar sequence thereof", the part "or an essentially similar sequence thereof" refers to the amino acid sequence of the native human Abl kinase domain containing mutations, including amino acid exchanges, amino add deletions and/or amino acid additions, that are not essential for the functionality of the kinase and its resistance to inhibition by STI571 or a salt thereof within the meaning of the term "functional" and "resistant" as defined hereinabove.

The expression "replaced by another amino acid" refers to the replacement of a certain natural amino acid by another natural amino acid.

The names of the amino acids are either written out or the one letter or three letter codes are used. Mutations are referred to by accepted nomenclature, e.g. "Ala380Thr" or "380 Ala→Thr" both indicating that alanine at position 380 is replaced by threonine.

SEQ ID NO:1 represents the cDNA coding for the native human Abl protein (human c-abl mRNA; GenBank Accession No.: X16416).

SEQ ID NO:2 represents the amino acid sequence of the native human Abl protein (human c-Abl; SwissProt Acc. No.: P00519).

Unless indicated otherwise, the number given for a certain amino acid refers to the numbering of the amino acids in SEQ ID NO:2. In an amino acid sequence that is essentially similar to the amino acid sequence of the native human Abl kinase domain within the meaning as defined above, the amino acids are numbered in accordance with the numbering of the amino acids in SEQ ID NO:2.

The term "isolated" means that the material is removed from its original environment (e.g., the natural environment if it is naturally occurring).

A "host cell", refers to a prokaryotic or eukaryotic cell that contains heterologous DNA that has been introduced into the cell by any means, e.g., electroporation, calcium phosphate precipitation, microinjection, transformation, viral infection, and the like.

DESCRIPTION OF THE INVENTION

In practicing the present invention, many conventional techniques in molecular biology, microbiology, and recombinant DNA are used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

In particular, the polypeptides of the present invention can be produced by recombinant DNA technology using techniques well-known in the art. Methods which are well known to those skilled in the art can be used to construct expression vectors containing the sequences encoding the polypeptides of the invention and appropriate transcriptional/translational control signals. A variety of host-expression vector systems can be utilized to express the polypeptides of the invention.

(1). The invention relates to an isolated polypeptide which comprises a mutated functional Abl kinase domain that is resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(2) The invention further relates in particular to an isolated polypeptide which comprises a mutated functional Abl kinase domain comprising the amino acid sequence of the native human Abl kinase domain or an essentially similar sequence thereof in which at least one amino acid is replaced by another amino acid, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(3) The invention especially relates to an isolated polypeptide which comprises a mutated functional Abl kinase domain comprising the amino acid sequence of the native human Abl kinase domain or an essentially similar sequence thereof in which at least one amino acid selected from Leu248, Glu255, Lys271, Glu286, Met290, Thr315, Tyr320, Asn322, Glu373, His375 and Ala380 is replaced by another amino acid, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(4) A preferred embodiment of the invention relates to an isolated polypeptide which comprises a mutated functional Abl kinase domain comprising the amino acid sequence of the native human Abl kinase domain or an essentially similar sequence thereof in which at least one amino acid selected from Leu248, Glu255, Lys271, Glu286, Met290, Tyr320, Asn322, Glu373, His375 and Ala380 is replaced by another amino acid, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(5) Another preferred embodiment of the invention relates to an isolated polypeptide which comprises a mutated functional Abl kinase domain comprising the amino acid sequence of the native human Abl kinase domain or an essentially similar sequence thereof in which at least one amino acid selected from Leu248, Lys271, Glu286, Met290, Tyr320, Asn322, Glu373, His375 and Ala380 is replaced by another amino acid, said mutated functional. Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(6) Another especially preferred embodiment of the invention relates to an isolated polypeptide which comprises a mutated functional Abl kinase domain comprising the amino acid-sequence of the native human Abl kinase domain or an essentially similar sequence thereof in which at least one amino acid selected from Glu255, Thr315 and Ala380 is replaced by another amino acid, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(7) Another very preferred embodiment of the invention relates to an isolated polypeptide which comprises a mutated functional Abl kinase domain comprising the amino acid sequence of the native human Abl kinase domain or an essentially similar sequence thereof in which at least one amino acid selected from Glu255 and Ala380 is replaced by another amino acid, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(8) Most preferably the invention relates to an isolated polypeptide-according to any one of the preceding paragraphs (2)-(7), wherein in the amino acid sequence of the native human Abl kinase domain or an essentially similar sequence thereof a single amino acid is replaced by another amino acid.

(9) The invention relates very especially preferred to an isolated polypeptide which comprises a mutated functional Abl kinase domain comprising the amino acid sequence of the native human Abl kinase domain or an essentially similar sequence thereof in which Glu255 is replaced by another amino acid, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(10) Most especially preferred the invention relates to an isolated polypeptide which comprises a mutated functional Abl kinase domain comprising the amino acid sequence of the native human Abl kinase domain or an essentially similar sequence thereof that contains at least one amino acid mutation selected from Glu255Val, Glu255Lys, Thr315Val, Thr315Leu, Thr315Met, Thr315Gln, Thr315Phe and Ala380Thr, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(11) In a further very preferred embodiment the invention relates to an isolated polypeptide which comprises a mutated functional Abl kinase domain comprising the amino acid sequence of the native human Abl kinase domain or an essentially similar sequence thereof that contains at least one amino acid mutation selected from Glu255Val, Thr315Val, Thr315Leu, Thr315Met, Thr315Gln, Thr315Phe and Ala380Thr, said mutated functional Abl kinase-domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)benzamide or a salt thereof.

(12) In another especially preferred embodiment the invention relates to an isolated polypeptide which comprises a mutated functional Abl kinase domain comprising the amino add sequence of the native human Abl kinase domain or an essentially similar sequence thereof that contains at least one amino add mutation selected from Thr315Leu, Thr315Met, Thr315Gln and Thr315Phe, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(13) Most preferably the invention relates to an isolated polypeptide according to any one of the preceding paragraphs (10)-(12), wherein the amino acid sequence of the native human Abl kinase domain or an essentially similar sequence thereof contains a single amino acid mutation.

(14) Preferred above all the invention relates to an isolated polypeptide which comprises a mutated functional Abl kinase domain comprising the amino acid sequence of the native human Abl kinase domain or an essentially similar sequence thereof that contains the amino acid mutation Glu255Val, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

(15) In a preferred embodiment the invention relates to an isolated polypeptide according to any one of the preceding paragraphs (2)-(14), wherein the amino acid sequence of the native human Abl kinase domain consists of amino acids 229-500 of SEQ ID NO:2.

(16) In another preferred embodiment the invention relates to an isolated polypeptide according to any one of the preceding paragraphs (2)-(15), said isolated polypeptide being a Bcr-Abl tyrosine kinase.

(17) In yet another preferred embodiment the invention relates to the use of an isolated polypeptide of any one of the preceding paragraphs (2) to (16) to screen for compounds which inhibit the tyrosine kinase activity of said polypeptide.

(18) The invention also relates to an isolated nucleic acid molecule comprising a nucleotide sequence that encodes a polypeptide according to any one of the preceding paragraphs (2)-(16).

(19) The invention further relates to the use of a nucleic acid molecule of the preceding paragraph (18) in the production of a polypeptide of any one of the preceding paragraphs (2) to (16) for use in screening for compounds which inhibit the tyrosine kinase activity of said polypeptide.

(20) The invention also relates to a recombinant vector comprising a nucleic acid molecule according to the preceding paragraph (18).

(21) The invention further relates especially to a recombinant vector according to the preceding paragraph (20), which is a recombinant expression vector.

(22) The invention also relates to a host cell comprising a recombinant vector according to the preceding paragraph (20) or (21).

Preferably the invention relates to an isolated polypeptide which comprises a mutated functional Abl kinase domain comprising the amino acid sequence of the native human Abl kinase domain in which at least one amino acid is replaced by another amino acid, said mutated functional Abl kinase domain being resistant to inhibition of its tyrosine kinase activity by N-[4-methyl-3-(4-pyridin-3-yl-pyrimidin-2-ylamino)-phenyl]-4-(4-methyl-piperazin-1-ylmethyl)-benzamide or a salt thereof.

Most preferred are the mutations described herein, which are present in patients who suffer from Philadelphia chromosome-positive leukemia and are resistant against treatment with STI571.

A preferred salt of STI571 is the methane sulfonate salt described in WO 99/03854.

Screening for compounds which inhibit the tyrosine kinase activity of the polypeptides of the invention may be done for example by using an isolated polypeptide of the invention in any in vitro tyrosine kinase phosphorylation assay known in the art and determining the potential of a compound to inhibit the tyrosine kinase activity of a polypeptide of the invention in such an assay.

High-throughput screening assays known in the art may be used to screen large compound libraries for compounds which inhibit the tyrosine kinase activity of the polypeptides of the invention.

Besides the random screening of large compound libraries, the polypeptides of the present invention may also be used in the following screening approach: The 3-dimensional structure of a polypeptide of the invention is determined by e.g. X-ray crystallography. The atomic coordinates of a polypeptide of the invention are then used to design a potential inhibitor. Said potential inhibitor is then synthesized and tested for its ability to inhibit the tyrosine kinase activity of the polypeptide of the invention in any in vitro tyrosine kinase phosphorylation assay.

EXAMPLES

The following Examples serve to illustrate the invention without limiting its scope.

Example 1

Methods:

Plasmids and Site Directed Mutagenesis:

The hybrid cDNA coding for HckAblSH1 was cloned by amplifying the respective DNA fragments from pUCΔNdeI/XbaIHck [Warmuth M. et al., J. Biol. Chem. 272, 33260-70 (1997)] and pcDNA3bcr-abl. These fragments were ligated blunt end to yield pUCΔNdeI/XbaIhckablSH1. Because of its relatively small size when compared to Bcr-Abl or c-Abl, this construct, hckAblSH1, allowed to introduce point mutations into the kinase domain of Abl by a one step cloning procedure. Point mutations were introduced into hckablSH1 using the QuickChange site directed mutagenesis protocol from Stratagene (La Jolla, Calif.). In order to introduce point mutations into Bcr-Abl, a KpnI/Eco47III-subfragment of Bcr-Abl containing the sequence coding for Bcr-Abl's kinase domain was cloned into pUCΔNdeI/XbaI engineered by site directed mutagenesis to contain an Eco47III site in the polylinker. After introduction of point mutations, this fragment was first recloned into pcDNA3abl. Thereafter, the 5' part of abl up to the KpnI site was substituted by Bcr coding sequences using a KpnI-fragment from pcDNA3bcr-abl. All mutations were confirmed by sequencing. For expression in Cos7 and 32D cells cDNAs were cloned into pApuro.

Cell Lines:

Parental 32D cells as well as 32D cells expressing Bcr-Abl and mutants thereof (32Dp210) were grown in Iscove's modified dulbeccos media (IMDM) supplemented with 10% FBS. COS7 cells were cultured in Dulbecco's modified eagle medium (DMEM) containing 4.5 g/l glucose) and supplemented with 10% FBS. All media and FBS were purchased from Gibco Life Technologies, Inc, Karlsruhe, Germany.

Transfection of Cells:

Cos7 cells were transfected using Effecten™ transfection reagent as to the guidelines of the manufacturer (Quiagen, Hilden, Germany). 32D cells were transfected by electroporation. Puromycin was used for selection at a concentration of 1 μg/ml.

Cell Lysis:

Cos7 cells were lysed as described recently [Warmuth M. et al., J. Biol. Chem. 272, 33260-70 (1997)]. For lysis, exponentially growing 32D cells were harvested and washed twice in cold PBS. For experiments evaluating the activity profile of STI571, cells were incubated with the indicated concentrations of inhibitor or with DMSO at a density of $5 \times 10^6$ cells/ml for 1.5-2 h. $10^7$ cells were lysed in 100 μl of lysis buffer containing 1% NP-40, 20 mM Tris (pH 8.0), 50 mM NaCl, and 10 mM EDTA, 1 mM phenylmethylsulfonylfluoride, 10 μg/ml aprotinin, 10 μg/ml leupeptin, and 2 mM sodium orthovanadate. After resuspension in lysis buffer, cells were incubated for 25 min on ice. Finally, unsoluble material was removed by centrifugation at 15,000 g. Clarified lysates were checked for protein concentrations using a BioRad protein assay.

Immunoprecipitation:

For immunoprecipitation 150 μl of standardized 32D cell lysate was diluted by addition of 450 μl of incubation buffer containing 20 mM Tris (pH 8.0), 50 mM NaCl, and 10 mM EDTA, 1 mM phenylmethylsulfonylfluoride, 10 μg/ml aprotinin, 10 μg/ml leupeptin, and 2 mM sodium orthovanadate and incubated with 5 μg of the indicated antibodies for 2 hours on a overhead rotor at 4° C. Sepharose A beads (Pharmacia Biotech Inc., Freiburg, Germany) were prepared by washing twice in IP buffer [0.1% NP-40, 20 mM Tris (pH 8.0), 50 mM NaCl, and 10 mM EDTA, 1 mM phenylmethylsulfonylfluoride, 10 μg/ml aprotinin, 10 μg/ml leupeptin, and 2 mM sodium orthovanadate] and added to each sample for 2 additional hours. Finally, the immunoprecipitates were washed three times in IP buffer, subsequently boiled in 2× sample buffer and prepared for SDS-PAGE.

Gel Electrophoresis and Immunoblotting:

Gel electrophoresis and immunoblotting were performed as described [Danhauser-Riedl S. et al., Cancer Res. 56, 3589-96 (1996); Warmuth M. et al., J. Biol. Chem. 272, 33260-70 (1997)] with some minor modifications. Proteins were routinely blotted on nitrocellulose membranes (Schleicher & Schuell, Dassel, Germany). Membranes were blocked in 5% milk powder for 1 h. Primary and secondary antibodies were diluted-1:500 to 1:5000 in TBS containing 1% milk powder. Proteins were detected using the ECL or ECL Plus detection system as recommended by the manufacturer (Amersham, Braunschweig, Germany).

Detection of Apoptosis by Flow Cytometry:

For assessing apoptosis induced by the various kinase inhibitors, cells were incubated with the indicated concentrations of STI571 at a density of $5 \times 10^4$ per ml. Apoptosis was routinely assessed by measuring the binding of FITC-conjugated Annexin V to the membranes of apoptosing cells. About $5 \times 10^4$ cells were taken at the indicated time points and washed once in PBS. Thereafter, cells were resuspended in 195 μl of Annexin V binding buffer and 5 μl of Annexin V-FITC (Bender MedSystems Diagnostics, Vienna, Austria) were added. Cells were mixed and incubated at room temperature for 10-20 min. Afterwards, cells were pelleted again, washed once and resuspended in 190 μl of Annexin V binding buffer. 10 μl of a 20 μg/ml propidium iodide stock solution were added and the ratio of Annexin V-positive to negative cells was determined by FACS-analysis using a Coulter EPICS XL 4-color cytometer.

Results:

Mutations to either Valine (V), Leucine (L), Isoleucine (I), Methionine (M), Glutamine (Q) or Phenylalanine (F) at position 315 and to either Serine (S), Cysteine (C) or Threonine (T) at position 380 were generated in a hybrid kinase, Hck-AblSH1, consisting of the SH2 and SH3 domain of Hck and the SH1/kinase domain of Abl. When expressed in Cos7 cells, these hybrid kinases and all mutants at position 315 and 380 showed a high spontaneous kinase activity, proving that these positions are not critical for ATP binding (Table 1). In marked contrast, when tested for inhibition by STI571, no inhibition was seen with up to 10 μM of compound for the mutants T315L, T315I, T315M, T315Q and T315F (Table 1), whereas HckAblSH1 wild-type (wt) could be inhibited with similar kinetics by STI571 as were found for Bcr-Abl (IC50 cellular tyrosine phosphorylation ($IC50_{CTP}$) approx. 0.5 μM). The mutants T315V and A380T retained some partial sensitivity but $IC50_{CTP}$ values were still higher than 10 μM. In contrast, the mutants A380S and A380C displayed sensitivity to STI571, which was comparable to HckAblSH1 wt (see Table 1 for summary).

TABLE 1

Influence of mutations of T315 and A380 of HckAblSH1 on kinase activity and inhibition by STI571

| | kinase activity | Inhibition by STI571 |
| --- | --- | --- |
| T315V | +++ | IC50 > 10 |
| T315L | +++ | CR |
| T315I | +++ | CR |
| T315M | ++++ | CR |
| T315Q | ++ | CR |
| T315F | ++ | CR |
| A380C | +++ | NS |
| A380S | +++ | NS |
| A380T | + | IC50 > 10 |

All data based on inhibition of cellular tyrosine phosphorylation of transiently transfected Cos7 cells determined by Western blot analysis using the monoclonal α-phosphotyrosine antibody PY99. IC50 values were determined using scion image software. Complete remission (CR) was defined as no detectable reduction of cellular tyrosine phosphorylation by 10 μM STI571. NS (normal sensitivity) = inhibition with similar kinetics as Hck-AblSH1 wt.

Our data identify positions 315 and 380 as critical gatekeepers for the binding pocket of STI571, which contribute to define the sensitivity of individual protein kinases towards STI571. For example, the STI571-insensitive receptor tyrosine kinase Flt-3, which has high homology to the c-Kit and the PDGF-R kinases, has a phenylalanine at the position homologous to T315, which would, based on our data, not be in accordance with STI571 binding. In a similar way, the resistance of most other kinases tested with STI571 could be explained.

In order to investigate whether and to what degree some of the above described point mutations of the gatekeeper position T315 are able to induce biological resistance towards STI571 we introduced into full length Bcr-Abl the mutations T315V, T315L, T315I, T315M, T315Q and T315F. When expressed in Cos7 cells all mutants displayed kinase activity close to or similar to wild-type Bcr-Abl (Bcr-ABLwt). If tested for inhibition by STI571, identical results were obtained as described for the corresponding mutations in HckAblSH1 (Table 2). Similar to Scr-Ablwt, expression of these mutants in 32D, an IL-3-dependent, hematopoietic cell line of murine origin, gave rise to cell lines growing IL-3 independently. Exposure of 32 DBcr-Ablwt cells to 1 or 10 μM STI571 lead to a rapid stop of proliferation and induction of apoptotic cell death in more than 90% of cells. On the contrary, if T315 mutant Bcr-Abl kinases, for example T315I, were expressed the block in proliferation and the induction of apoptosis caused by 1 μM STI571 were completely abolished (Table 2) and the effects of STI571 seen at 10 μM were reduced to levels found in control experiments using parental 32D cells grown in the presence of IL-3. Phosphotyrosine blots of samples of cells expressing either wt or mutant Bcr-Abl proteins confirmed that mutations at position 315 completely abolished the effect of STI571 on Abl auto- and substrate phosphorylation, with the exception of T315V which was still to some degree inhibited by STI571 but displayed a similar biological phenotype as the other mutants (Table 2). This suggests that the reminder biological activity of STI571 at 10 μM was rather due to cytotoxicity than to a reminder sensitivity of the mutants or cross-reaction of STI571 with another tyrosine kinase. In summary, all mutations lifted the IC50 for inhibition of proliferation ($IC50_{IOP}$) from 0.09 to approximately 7.5 μM and for inhibition of survival ($IC50_{IOS}$) from 0.5 to more than 10 μM (Table 2). Taken together, these data show that mutations of "molecular gatekeeper" positions as described above are able to confer complete biological resistance towards STI571 in a cell culture model.

TABLE 2

Biochemical and biological characterization of mutations of T315 in Bcr-Abl to amino acids with longer side chains

| mutant | kinase activity | IC50 (μM) cellular kinase tyrosine phosphorylation Cos7 | 32D | Induction of growth factor-independent growth in 32D | IC50 (μM) apoptosis 32D | IC50 (μM) proliferation 32D |
|---|---|---|---|---|---|---|
| (32D) | | | | | >107.5 | |
| wt | +++ | 0.25 | 0.25 | yes | 0.5 | 0.09 |
| T315V | +++ | >10 | >10 | yes | >10 | 7.5 |
| T315L | ++++ | c.r. | c.r. | yes | >107.5 | |
| T315I | +++ | c.r. | c.r. | yes | >107.5 | |
| T315M | ++++ | c.r. | c.r. | yes | >10 | 7.5 |
| T315Q | +++ | c.r. | c.r. | yes | >10 | 7.5 |
| T315F | +++ | c.r. | c.r. | yes | >10 | 7.5 | c.r: complete remission (no detectable reduction of cellular tyrosine phosphrylation by 10 μM STI571)

Example 2

STI571 inhibits the Abl tyrosine kinase with an $IC_{50}$ of 0.025 μM for purified Bcr-Abl and c-Abl but not the fins or the Src family kinases. The mechanism of inhibition is through competitive inhibition of ATP binding. To better understand the mechanism of specificity of the tyrosine kinase inhibitor the Abl kinase was compared to a model of the Lck kinase domain. This model predicts the following sites are critical for STI571 association: L248, Y320, N322, E373, H375 and A380. Each of these residues were changed to the corresponding residue in Src or fins and $IC_{50}$ values for STI571 with each mutant were determined. L248A and H375L yielded kinase inactive mutants, Y320K, N322S, E373N and A380G had $IC_{50}$ values identical to wild type Abl. A380T, however, demonstrated an $IC_{50}$ of 0.34 μM suggesting that STI571 bound less efficiently when a larger residue replaced the alanine. Recent crystallization of the Abl kinase domain with a related inhibitor shows that the configuration of the activation loop of the Abl kinase domain differs significantly from that of the Src family kinases. This structure identifies K271, E286, M290, T315, M318 and D381 as critical contacts of STI571. All of these residues are conserved between Src and Abl. The last two of these bind STI571 via their peptide backbone, thus mutants in these residues cannot be created. The remainder of the residues were mutated to residues lacking the potential for hydrogen bonding and $IC_{50}$ values were determined. K271R, E286L and M290A were kinase inactive. T315V had an $IC_{50}$ value of 0.35 μM, which is consistent with the crystal structure of the Abl kinase domain which predicts that the side chain of T315 forms a critical hydrogen bond with STI571.

Example 3

A group of 32 patients who are either refractory to treatment with STI571 or who relapsed whilst being treated were investigated. The median duration of therapy was 95 days; prior to STI571 treatment, two patients were in chronic phase, nine in accelerated phase, 20 in myeloid and, and one in lymphoid blast crisis of the disease. Reverse transcriptase-polymerase chain reaction (RT-PCR) products specific for the Bcr-Abl tyrosine kinase domain were sequenced (Heminested RT-PCR was performed to amplify the sequence specifically coding for the Bcr-Abl tyrosine kinase: $1^{st}$ step B2B ACAGAATTCCGCTGACCATCAATAAG and A7–AGACGTCGGACTTGATGGAGAACT; $2^{nd}$ step FA4+ AAGCGCAACAAGCCCACTGTCTAT and A7–).

An acquired A→T point mutation at position 58802 (GeneBank accession number U07563, locus HSABLGR3)—which results in a Glu255Val substitution—was detected in one patient. Restriction analysis of cDNA and genomic DNA (RT-PCR and genomic PCR were performed using primers A4+TCACCACGCTCCATTATCCA, A4–CTTCCACACGCTCTCGTACA; Mnl I restriction digest of PCR products; removal of an Mnl I restriction site as the result of the point mutation A58802T) was used to confirm the presence of the mutation and to track it during the course of treatment. Only wild-type Abl sequence was present before the STI571 therapy. The patient was treated with STI571 in late chronic phase, went into complete hematologic remission, but progressed to blast crisis after five months. Reactivation of Bcr-Abl was confirmed by CrkI immunoblotting [K. Senechal, Mol. Cell. Biol. 18, 5082 (1998)]. The relative proportion of phosphorylated CrkI (reflecting active Bcr-Abl) was 49% before STI571 therapy, 24% at day 27, 28% at day 83, and 77% at the time of clinical resistance at day 166. The biological significance of the Glu255Val change is determined by an Abl autophosphorylation assay. STI571 inhibits wild-type Abl with an $IC_{50}$ of 0.025 μM. The mutation leads to a virtual insensitivity to STI571, with an $IC_{50}$ of >5 μM.

Example 4

The Bcr-Abl kinase domain from cells obtained from 12 CML and Ph+ acute leukemia patients who relapsed while receiving STI571 was sequenced. A functional point-mutation in the kinase domain in one case was identified. This was a G→A change that results in a Glu→Lys substitution at position 255 of Abl.

Example 5

Patients and Sample Preparation:

Thirty bone marrow samples from 21 patients with Ph+ ALL who were enrolled into consecutive "Phase II study to determine the safety and anti-leukemic effect of STI571 in adult patients with Ph+ acute leukemias" were analyzed. According to the study protocol, these patients had relapsed ALL or were refractory after at least 2 cycles of standard chemotherapy. From all of the patients, samples were obtained before beginning STI571 treatment: 13 of these samples were from individuals who later were classified as good responders to STI571 (Nos. 1-13, sensitive, S) including 12 patients with hematological complete remission (CR) and one patient with partial remission (PR) but complete peripheral hematological recovery (No. 1). Eight samples were collected from individuals who later were found not to respond to STI571 (Nos. 14-21, primarily resistant, R) including 6 patients without any hematological response, one with cytoreduction in the bone marrow but persistent peripheral leukemic cells (No. 20) and another with PR but incomplete peripheral hematological recovery (No. 16). Matched bone marrow samples from 9 patients (Nos. 1-5 and Nos. 14-17) were also obtained while they were on treatment with STI571. Mononuclear cells were separated by density gradient centrifugation through Ficoll-Hypaque (Biochrom, Berlin, Germany). Total RNA was extracted using the acid guanidium/phenol/chloroform method with minor modifications. [Puissant C. and Houdebine L. M., Biotechniques 8, 148-149 (1990)]. Only samples with leukemic blast cell infiltration of more than 80% were included into the analysis.

Reverse transcription polymerase chain reaction and sequencing analysis: One microgram of total RNA was used for reverse transcription (RT) by Superscript II RT (Life Technologies, Grand Island, N.Y.) according to standard protocols, Primers specific for the ATP binding site of ABL including the loop were designed using gene bank information G16382056: ATP-F 5'-GCG CAA CAA GCC CAC TGT CT-3'; ATP-R 5'-GCA CTC CCT CAG GTA GTC CA-3' and LOOP-F 5'-TGG ACT ACC TGA GGG AGT GC-3'; LOOP-R 5'-CGG TAG TCC TTC TCT AGC AGC-3'. Oligonucleotides were synthesized by Life Technologies. Polymerase chain reaction (PCR) was performed as described previously [Hofmann W. K. et al., Leuk. Res. 25, 333-338 (2001)] using an annealing temperature of 58° C. PCR-products were separated on a 2% agarose gel containing 0.3 mg/ml ethidium bromide and purified using the QIAquick purification system (Qiagen, Valencia, Calif.) according to the manufacturers protocol. The purified DNA was directly sequenced in both directions (sense and antisense) by the ABI PRISM dye terminator cycle sequencing reaction (Perkin-Elmer, Foster, Calif.).

Results:

Analysis of the sequence of the ATP binding site revealed a single point mutation at nucleotide 1127 (GI6382056) changing a G to an A resulting in a substitution at codon 255 of Lys (mutant) for a Glu (wild-type). This mutation was found in 6 samples from patients after they were treated with STI571 (Nos. 1, 2, 4, 5, 15, 16) but mutations were not found in any other sample including the matched samples from the patients before beginning treatment with STI571 (Table 3). The change was verified by sequencing from both the sense and antisense directions. In addition, one sample (No: 17) from a patient with an aberrant CALL had a single point mutation at nucleotide 1308 changing a C to T resulting in a substitution at codon 315 of isoleucine (mutant) for a threonine (wild-type). This sample was unusual because the cells also expressed CD33, a cell surface protein expressed on myeloid cells.

Our data strongly suggest that E255K developed during treatment with STI571. Our analysis of matched samples found, that none of the samples from untreated patients (including sensitive patients and those with primary resistance) had this mutation. In contrast, six of 9 samples (67%) from these patients undergoing treatment with STI571 had this substitution at E255. The overall frequency of mutations in the ATP binding site was 7 of 9 (78%) in our paired bone marrow samples from patients undergoing therapy with STI571.

TABLE 3

Matched bone marrow samples: Development of mutations in the Region coding for the ATP binding site of ABL during treatment of Ph+ ALL with STI571.

| No. | Diagnosis | ABS status prior to treatment with STI571 | Response to STI571 | ABS status after treatment with STI571 |
|---|---|---|---|---|
| 1 | Ph+ cALL | Wild type | PR | E255K |
| 2 | Ph+ cALL | Wild type | CR | E255K |
| 3 | Ph+ cALL | Wild type | CR | Wild type |
| 4 | Ph+ cALL | Wild type | CR | E255K |
| 5 | Ph+ cALL | Wild type | CR | E255K |
| 14 | Ph+ cALL | Wild type | no | Wild type |
| 15 | Ph+ cALL | Wild type | no | E255K |
| 16 | Ph+ pre B-ALL | Wild type | PR | E255K |
| 17 | Ph+ cALL, CD33+ | Wild type | no | T315I |

ABS, ATP binding site; PR, partial remission; CR, complete remission; Ph+ cALL, Philadelphia chromosome positive, common ALL (CD10+).

What is claimed is:

1. A method of detecting STI571 resistance prior to clinical relapse of a subject during STI571 therapy, comprising:
   obtaining a sample from a subject undergoing STI571 therapy;
   detecting a mutation in an amino acid sequence of the Abl kinase domain of a Bcr-Abl polypeptide in the sample obtained from the subject compared to the Abl kinase domain of SEQ ID NO:2, wherein the mutation confers resistance to kinase inhibition by STI571, thereby detecting STI571 resistance prior to clinical relapse of the subject.

2. The method of claim 1, wherein the difference in the amino acid sequence is an amino acid substitution at position 315.

3. The method of claim 1, wherein detecting a mutation in the Abl kinase domain of the Bcr-Abl polypeptide comprises:
   determining the sequence of a nucleic acid encoding the Abl kinase domain; and
   comparing the amino acid sequence encoded by the nucleic acid with the amino acid sequence set forth as SEQ ID NO: 2,
   wherein a difference in the amino acid sequence of the Abl kinase domain from the sample from the amino acid sequence set forth as SEQ ID NO: 2 detects an STI571 resistant Abl kinase domain.

4. The method of claim 1, wherein the difference in the amino acid sequence is an amino acid substitution at position 255.

5. The method of claim 4, wherein the method comprises detection of an A to T point mutation that results in the substitution of valine for glutamic acid at position 255 or a G to A point mutation that results in the substitution of lysine for glutamic acid at position 255.

6. The method of claim 3, wherein the method comprises detection of a C to T point mutation that results in a substitution of isoleucine for threonine at position 315.

7. The method of claim 1, wherein determining the nucleic acid sequence comprises reverse transcriptase polymerase chain reaction.

8. The method of claim 1, wherein determining the nucleic acid sequence comprises DNA sequencing.

9. The method of claim 1 wherein the tumor is a leukemia.

10. The method of claim 9, wherein the leukemia is myelogenous leukemia.

11. The method of claim 1, wherein detecting a mutation in an Abl kinase domain of the Bcr-Abl polypeptide comprises:
   determining the sequence of an Abl kinase domain in a sample from the subject; and
   comparing the amino acid sequence of the Abl kinase domain with the amino acid sequence set forth as SEQ ID NO: 2,
   wherein a difference in the amino acid sequence of the Abl kinase domain from the sample from the amino acid sequence set forth as SEQ ID NO: 2 detects an STI571 resistant Abl kinase domain.

12. The method of claim 11, wherein the difference in the amino acid sequence is an amino acid substitution at position 315.

13. The method of claim 12, wherein the substitution is a substitution of isoleucine for threonine at position 315.

14. The method of claim 11, wherein the difference in the amino acid sequence is an amino acid substitution at position 255.

15. The method of claim 14, wherein the substitution is a substitution of valine for glutamic acid or lysine for glutamic acid at position 255.

16. The method of claim 11, wherein the tumor is a leukemia.

17. The method of claim 16, wherein the leukemia is myelogenous leukemia.

18. A method of detecting STI571 resistant mutation in a subject, comprising:
    obtaining a sample from the subject;
    detecting a mutation in an amino acid sequence of the Abl kinase domain of a Bcr-Abl polypeptide in the sample obtained from the subject compared to the ABl kinase domain of SEQ ID NO:2, wherein the mutation is an amino acid substitution at position 315, 248, 255, 271, 286, 290, 315, 320, 322, 373, 375 or 380 of the Abl kinase domain that confers resistance to kinase inhibition by STI571, thereby detecting an STI571 resistant mutation in the subject.

19. The method of claim 18, wherein the substitution is a substitution of isoleucine for threonine at position 315.

20. The method of claim 18, wherein the substitution is a substitution of valine for glutamic acid or lysine for glutamic acid at position 255.

21. The method of claim 18, wherein detecting a mutation in an Abl kinase domain of the Bcr-Abl polypeptide, comprises:
    determining the sequence of an Abl kinase domain in a sample from the subject; and
    comparing the amino acid sequence of the Abl kinase domain with the amino acid sequence set forth as SEQ ID NO: 2,
    wherein a difference in the amino acid sequence of the Abl kinase domain from the sample from the amino acid sequence set forth as SEQ ID NO: 2 indicates the presence of mutant Abl kinase domain in the subject.

22. The method of claim 18, wherein the subject has a tumor.

23. The method of claim 22, wherein the tumor is a leukemia.

24. The method of claim 23, wherein the leukemia is myelogenous leukemia.

25. The method of claim 18, wherein the subject is undergoing STI571 therapy and the method is used to detect the presence of the STI571 resistant Abl kinase domain mutation prior to clinical relapse.

* * * * *